United States Patent [19]

Young et al.

[11] 4,212,897

[45] Jul. 15, 1980

[54] ADHERENT CONTROLLED RELEASE PESTICIDES USING ORGANOPOLYSILOXANES

[75] Inventors: Robert W. Young, New York, N.Y.; Samuel Prussin, Carmel, Calif.; Norman G. Gaylord, New Providence, N.J.

[73] Assignee: The Young, Prussin, MGK, J.V., New York, N.Y.

[21] Appl. No.: 927,630

[22] Filed: Jul. 24, 1978

Related U.S. Application Data

[63] Continuation of Ser. No. 696,274, Jun. 15, 1976, abandoned.

[51] Int. Cl.$^2$ .................. A61K 31/695; A01N 17/08
[52] U.S. Cl. ........................................... 427/2; 427/4; 424/77; 424/78; 424/184; 424/DIG. 6; 424/DIG. 10; 71/DIG. 1
[58] Field of Search ........ 424/184, DIG. 10, DIG. 6, 424/77, 78, 186; 71/DIG. 1, DIG. 2; 43/136; 427/2, 4

[56] References Cited

U.S. PATENT DOCUMENTS

| | | | |
|---|---|---|---|
| 2,681,878 | 6/1954 | Kauppi | 424/184 |
| 2,923,095 | 2/1960 | Bordeaux et al. | 427/4 X |
| 2,988,473 | 6/1961 | Mallis | 424/184 |
| 3,151,969 | 10/1964 | Stevens | 424/186 |
| 3,248,409 | 4/1966 | Bluestein | 424/186 |
| 3,375,163 | 3/1968 | Whitney | 424/184 |
| 3,470,292 | 9/1969 | Marschner | 424/184 |
| 3,480,653 | 11/1969 | Pande | 260/429.9 |
| 3,481,768 | 12/1969 | Gowdy | 427/212 |
| 3,590,118 | 6/1971 | Conrady | 424/78 |
| 3,641,239 | 2/1972 | Mohrlok | 424/184 |
| 3,836,647 | 9/1974 | Lange | 424/184 |
| 3,953,591 | 4/1976 | Snyder | 424/78 |

OTHER PUBLICATIONS

C & EN, Oct. 15, 1956, pp. 5060–5063.
Chemistry & Technology of Silicones, Noll, 1971, pp. 399, 514 & 515.

*Primary Examiner*—Sam Silverberg
*Attorney, Agent, or Firm*—Roylance, Abrams, Berdo & Farley

[57] ABSTRACT

There are disclosed methods and compositions for the controlled release of insecticides by using a mixture consisting of (a) an organopolysiloxane containing hydroxyl groups or functional groups which are hydrolyzable to hydroxyl groups, (b) a hydrolyzable organic titanium compound or a partial hydrolyzate thereof, and (c) a pesticide, e.g., an insecticide.

19 Claims, No Drawings

ADHERENT CONTROLLED RELEASE PESTICIDES USING ORGANOPOLYSILOXANES

This is a continuation of application Ser. No. 696,274, filed June 15, 1976 now abandoned.

This invention relates to methods and compositions for the controlled release of bioactive agents and, more particularly, to the controlled release of pesticides, such as insecticides.

The utilization of bioactive agents such as pesticides, e.g., insecticides, herbicides and fungicides has become an important fact of life. However, these materials are generally effective only as long as they persist on the substrate to which they are applied.

The basic motivation underlying the modern development of controlled release pesticidal materials has been to extend the duration between applications and thus increase the efficiency and hence economy of control. Controlled release of pesticides permits extended time intervals between treatments and reduction of the dosage, thus reducing environmental impact. Thus, from an ecological standpoint, controlled release of pesticides enhances the lifetime of a non-persistent agent at the site of treatment while maintaining the preferred property of rapid detoxification in the environment surrounding the controlled release pesticide.

The desired controlled release of pesticides has previously been achieved by their incorporation within a polymeric matrix, e.g., encapsulation wherein a pest control agent is surrounded by an enveloping polymeric wall that permits loss through diffusion, permeation or degradation; dispersion of the pesticide in an elastomer or a plastic wherein the pesticide is released through leaching or diffusion; and the chemical combination of the pesticide with a polymer in such a manner that the appended pesticide slowly breaks off the polymeric backbone upon exposure to the pest infested environment. However, the prior art approaches fall short of the desired goal in that there is not adequate provision for the adhesion of the pesticide within the polymeric matrix to the substrate. This permits the removal or transfer of the material from the substrate as a result of physical contact, wind, rain or other atmospheric conditions.

One object of the present invention is to provide a process for the controlled release of bioactive agents such as pesticides.

Another object of the present invention is to improve the adhesion of such an agent to suitable substrates and thus to increase its effective lifetime.

Another object of the present invention is to provide stable compositions which after application to a suitable substrate and exposure to the atmosphere, undergo in situ chemical reaction resulting in adherent insecticides with controlled release characteristics.

A further object of the present invention is to provide novel compositions containing reactive polysiloxanes, adhesion promoting, crosslinking organic titanium compounds and insecticides.

These and other objects of the present invention are achieved by using a mixture consisting of (a) an organopolysiloxane containing hydroxyl groups or functional groups which are hydrolyzable to hydroxyl groups, (b) a hydrolyzable organic titanium compound or a partial hydrolyzate thereof, and (c) an insecticide.

The organopolysiloxanes suitable for use in the practice of the present invention are well known in the art and contain the structural unit

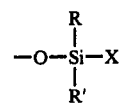

wherein X is a hydroxyl radical or a hydrolyzable radical such as alkoxy, acyloxy, hydrogen, halogen and the like and R and R' are oxygen (i.e., the group —O—) or non-hydrolyzable hydrocarbon, substituted hydrocarbon or heterocyclic radicals and are the same or different. When R and R' are hydrocarbon radicals, they may be acyclic or cyclic, saturated or unsaturated and include aliphatic radicals such as methyl, ethyl, vinyl, propyl, allyl, butyl, crotyl, hexyl, decyl, dodecyl, hexadecyl, octadecyl, octadecenyl radicals and the like as well as halogenated or other substituted aliphatic radicals, aromatic radicals such as phenyl, biphenyl, phenoxyphenyl and naphthyl radicals as well as halogenated and other substituted aromatic radicals, aralkyl radicals such as benzyl and phenylethyl radicals, alkylaryl radicals such as tolyl and xylyl radicals, cycloaliphatic radicals such as cyclopropyl, cyclopentyl, cyclopentenyl, cyclohexyl and cyclohexenyl radicals and heterocyclic radicals such as furfuryl radicals.

The organopolysiloxanes may be linear, branched or both linear and branched and the X radicals may be terminal end groups or may be situated at other sites in the polysiloxane chain. The number of X radicals may range from one radical per polysiloxane molecule up to 30 weight percent of the total organopolysiloxane molecular weight.

The polysiloxane may be predominantly a monoorganopolysiloxane, a diorganopolysiloxane, a copolymer containing monoorganosiloxane units and diorganosiloxane units, a copolymer containing triorganosiloxane units and $SiO_2$ units and the like. Notwithstanding the predominant structure, the organopolysiloxane may contain varying amounts of the other structural units in addition to hydroxyl radicals or radicals hydrolyzable thereto.

The polysiloxanes suitable for use in the practice of the present invention are well known in the art and may be prepared by various procedures including controlled hydrolysis of appropriate precursors as well as ring opening polymerization of cyclic organopolysiloxanes.

The controlled hydrolysis and cohydrolysis of $RSiX_3$, $R_2SiX_2$, $R_3SiX$ and $SiX_4$, where X is a hydrolyzable radical as previously defined, yields organopolysiloxanes containing monoorganosiloxane, diorganosiloxane, triorganosiloxane and $SiO_2$ units, respectively. The relative proportions of said units in the organopolysiloxane are determined by employing the appropriate ratios of hydrolyzable precursors. In order to be useful in the practice of the present invention, the resultant organopolysiloxane must be readily soluble or dispersible in organic solvents and contain residual hydroxyl or hydrolyzable radicals.

The polymerization of cyclic organopolysiloxanes provides another route to the preparation of organopolysiloxanes containing hydroxyl or hydrolyzable radicals which may be employed in the practice of the present invention. These and other methods of preparation are set forth in K. A. Andrianov, "Metalorganic Polymers", Interscience Publishers, New York, 1965, Chapter III, pages 109–275, the disclosures of which are incorporated herein by reference.

Polysiloxanes which are at an intermediate stage of polymerization in that they contain hydroxyl radicals which, upon application of heat, may undergo condensation to a more advanced stage of polymerization or in that they contain hydrolyzable groups which upon further hydrolysis may proceed to a more advanced stage of polymerization are suitable for use in the practice of the present invention if they have not been rendered insoluble in organic solvents.

The organopolysiloxanes may be fluids of low or high viscosity or even solids. The physical appearance of the polysiloxane is dependent upon the nature of the R and R' radicals, the presence of linear or branched structures as well as the molecular weight. Notwithstanding the physical appearance of the polysiloxane, the important requirement for utility in the practice of the present invention is the presence of hydroxyl radicals or radicals hydrolyzable thereto. Mixtures of such polysiloxanes are suitable for use in the present invention.

The hydrolyzable titanium compounds which are suitable for use in the practice of the present invention are the tetraesters, tetraanhydrides and tetraamides of orthotitanic acid.

The titanium tetraesters have the formula:

$$Ti(OR)_4$$

where R is an aliphatic hydrocarbon radical of less than about 20 carbon atoms and may be saturated or unsaturated and acyclic or cyclic. Thus, R may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. Titanium orthoesters where R is the same or mixed are suitable for use in the present invention. Partially hydrolyzed orthoesters may also be used if the hydrolysis has not rendered them insoluble in organic solvents and they still retain alkoxy groups.

The titanium tetraanhydrides have the formula:

$$Ti(OCOR')_4$$

where R' is an aliphatic hydrocarbon radical of less than about 20 carbon atoms and may be saturated or unsaturated and acyclic or cyclic. Thus, R' may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. The anhydrides or acylates may also be prepared from aliphatic acids which contain more than one carboxyl group, such as maleic acid, fumaric acid, etc. Titanium acylates where R' is the same or mixed are suitable for use in the present invention. Mixed alkoxytitanium acylates are also useful. These are prepared by the reaction of a tetraester with an acid or anhydride or of a tetraanhydride with an alcohol under anhydrous conditions. Partially hydrolyzed acylates may also be used.

The titanium tetraamides have the formula:

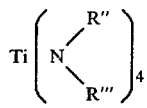

where R" is hydrogen, alkyl or aryl and R''' is alkyl or aryl. The alkyl groups may be saturated or unsaturated and acyclic or cyclic and include methyl, ethyl, propyl, butyl, amyl, octyl, stearyl, oleyl, etc. groups.

The titanium polymers prepared by partial hydrolysis of the monomeric titanium orthoesters, acylates and amides, per se or in admixture, as well as by partial hydrolysis of mixed orthoesters, acylates and amides may also be used in the practice of the present invention.

While hydrolyzability is a general characteristic of the tetraesters, tetraanhydrides and tetraamides of orthotitanic acid which may be used in the practice of the present invention, the rate of hydrolysis is a function of the nature of the hydrocarbon substituent. Thus, the presence of methyl, ethyl and other lower alkyl substituents results in rapid hydrolysis while higher alkyl substituents result in slower hydrolysis. In the latter case it is possible to use water as a diluent or dispersing medium during the preparation and handling of the active compositions, and as the hydrolyzing reactant as the composition is applied or after it is applied to the substrate.

An alternative approach to delayed hydrolysis is the use of an organic titanium chelate. The chelates which are suitable for use in the practice of the present invention are either water soluble or solvent soluble and hydrolyze slowly in aqueous systems per se or when the pH is changed or the temperature is raised.

The titanium chelates are derivatives of bi- or multifunctional compounds in which one of the functional groups is usually hydroxyl or enolic carbonyl and the other group is hydroxyl, carboxyl, carbonyl or amino. Thus, the titanium chelates are derivatives of glycols, hydroxy acids, dicarboxylic acids, diketones, ketoesters or alkanolamines. Representative chelates include chelates of 2-methylpentane-2,4-diol, 2-ethylhexane-1,3-diol, 2-methylpentane-1,3-diol, 2-propylheptane-1,3-diol, lactic acid, glycolic acid, citric acid, tartaric acid, hydroxystearic acid, oxalic acid, acetylacetone, ethyl acetoacetate, diethanolamine, triethanolamine and the like.

The titanium chelates are generally prepared by the reaction of a titanium alkoxide such as tetraisopropyl titanate and the appropriate bi- or multifunctional compound. The preparation and properties of the titanium chelates are disclsed in Kirk-Othmer Encyclopedia of Chemical Technology, John Wiley & Sons, New York, 2nd Edition, Volume 20, pages 464–468 (1969). The preparation of aqueous solutions of the titanium chelates is described in "Tyzor Organic Titanates", E. I. duPont de Nemours & Co., Organic Chemicals Department, Technical Bulletin D-5258. The disclosures of each of the hereinabove identified references are incorporated herein by reference.

The preferred compositions of the present invention contain organopolysiloxane and titanium compounds in weight ratios ranging from 10/90 to 95/5.

The use of titanates as catalysts for the polymerization of hydroxyl-containing polymers including organopolysiloxanes is well known to those skilled in the art.

The use of titanates permits more rapid cures at lower temperatures than could otherwise be obtained.

The use of organic titanates to catalyze the cure of organopolysiloxanes to impart water repellency to leather is disclosed in U.S. Pat. Nos. 2,672,455 and 2,970,126. A process for preparing cured polysiloxane coatings, particularly useful in water-proofing fabrics, as disclosed in U.S. Pat. No. 2,732,320, involves treatment of the fabric with a solution containing a polymerizable organopolysiloxane and an alkyl titanate at room temperature, followed by baking at a temperature which is substantially higher but below 150° C. The use of organic titanates in providing rapid, low temperature curing of silicone resins for water repellent finishes has been reviewed by G. W. Nadaras, Journal of the Society of Dyers and Colourists, 74, 835 (1958). Water repellent compositions containing titanate catalyzed silicones are also disclosed in U.S. Pat. No. 2,769,732. The disclosures of each of the hereinabove identified references are incorporated herein by reference.

The use of organic titanates to modify solid surfaces for the purpose of improving adhesion is also well known art. The titanates are generally applied to the solid surface, such as that of glass, metals and polymers, and permitted to hydrolyze to form a primed surface for the subsequent application of films and coatings (U.S. Pat. Nos. 2,768,909 and 2,838,418). Organic titanates have been applied to solid surfaces to serve as prime coats for binding organopolysiloxanes (U.S. Pat. No. 2,751,314).

It is surprising, in view of the disclosures of the prior art, that in the presence of moisture, at ambient temperature, an organic titanate can simultaneously catalyze and/or crosslink an organopolysiloxane and promote adhesion to a solid surface. It is even more surprising that an insecticide can be incorporated in such a reactive system and the resultant composition, upon application to a suitable surface and reaction with moisture at ambient temperature, provide an adherent, controlled release insecticide.

Insecticides which may be used in the practice of this invention include any of the compounds well known in the art for use as insecticides such as those set forth in Chemical Week, June 21, 1972, pages 39-64; Chemical Week, July 26, 1972, pages 19-41; and Commercial and Experimental Organic Insecticides (1974 Revision), Entomological Society of America, Special Publication 74-1, October 1974. Some common insecticides which may be used include the following:

1-naphthyl methylcarbamate (SEVIN)
pyrethrins
malathion
parathion
methylparathion
phorate
toxaphene
chlordane
Dursban
Baygon
DDT
Diazinon The insecticides which may be used in the practice of this invention also include bacterial insecticides such as *Bacillus popilliae* and *Bacillus thuringiensis* and viral insecticides such as the Heliothis virus. These have been described in Chemical & Engineering News, 35, No. 30, 18 (July 28, 1975), the disclosures of which are incorporated herein by reference.

The insecticide is included in the composition in an amount sufficient to exert an insecticidal action on the immediate environment surrounding the substrate. The amount of insecticide will be dependent upon several factors such as the composition and thickness of the cured polymeric matrix, the nature of the insecticide, i.e., liquid or solid, the presence of active hydrogen functionality, the duration of insecticidal action desired, etc. The optimum amount of insecticide to be included may readily be determined by those skilled in the art. Generally, from about 1 part by weight of insecticide to 0.5 to 1000 parts of the combined weight of polysiloxane and titanium compound is satisfactory.

The compositions of this invention may include volatile diluents such as aliphatic or aromatic hydrocarbons, e.g., Stoddard Solvent, mineral spirits, B&P naphtha, cyclohexane, petroleum ether, benzene, toluene, xylene, etc., halogenated hydrocarbons such as perchloroethylene and fluorocarbons or volatile fluid polysiloxanes such as dimethylpolysiloxane fluids. The compositions may be prepared by merely admixing the various components. Before admixing, the components may be dispersed or dissolved in a diluent such as previously described. The compositions may also be prepared in aqueous media when slowly hydrolyzing and/or stable components are present.

The compositions of this invention may be applied to a large number of substrates. The substrate should be one which contains active hydrogen atoms which provide sites for coupling with the polysiloxane-titanium compound system, e.g., hydroxyl groups, amino groups, etc. Thus, various plants such as ornamental bushes, trees, flowers, greenhouse plants, lawns, crops (e.g., wheat, corn, soy beans, barley, oats, cotton, jute, sisle), fruits, vegetables, berry bushes, nut trees, olive trees, fig trees, grape vines; various animals such as household pets (e.g., cats, dogs), farm animals such as dairy cattle, beef cattle, horses, sheep, chickens, turkeys, swine, goats, zoo animals, etc. Non-plant and animal uses include spraying surfaces of structures such as buildings and various rooms in buildings, such as kitchens, bathrooms, closets including wood or plaster board walls and floor tile to protect against roaches, termites, flying insects, rug insects, ants, etc. Various containers such as bags and cardboard or wooden boxes may also serve as substrates in accordance with the practice of this invention.

The compositions of this invention may be applied to the substrate by brushing, spraying, dipping or any other known technique for applying a fluid composition to a solid substrate. It may be applied in the form of an aerosol mist or fog, propelled by conventional pressurized volatile halohydrocarbon, hydrocarbon or compressed gas propellants, an air propelled mist blower, a fog generator, or other suitable means.

Although this invention should not be limited thereby, it is believed that upon application of the compositions of this invention to a suitable substrate in an ambient atmosphere, evaporation of the volatile diluent, if any is present, and exposure to atmospheric moisture results in the hydrolysis of the titanium compound, followed by condensation of the TiOH groups generated thereby with the SiOH groups present or generated by hydrolysis on the organopolysiloxane. Since the titanium compound is polyfunctional, the reaction of its hydrolyzate with the hydroxyl-containing polysiloxane converts the latter into a higher molecular weight, probably crosslinked, polymer containing entrapped or occluded insecticide. Simultaneously, the hydrolyzed titanium compound promotes the adhesion of the polysiloxane and the insecticide entrapped or occluded therein to the substrate. Adhesion to the substrate is due at least in part to the fact that the polysiloxane-titanium compound matrix is coupled to the substrate by reaction through active hydrogen atoms on the substrate. In this manner, the insecticide is held on the substrate to such an extent that it cannot be physically brushed off, blown off or washed off by rain. Further, as a result of its entrapped condition the rapid evaporation, sublimation or extraction of the insecticide is retarded. However, due to the permeability of the polysiloxane to organic compounds, said evaporation or sublimation is not completely inhibited, resulting in controlled release of the insecticide.

When water is present in the compositions of this invention, said water is generally added shortly before application of the composition to a suitable substrate, and hydrolysis of the titanium compound may begin before or during application to said substrate. However, hydrolysis continues after said application and is followed by condensation of the TiOH groups generated thereby with the SiOH groups present or generated by hydrolysis on the organopolysiloxane.

When a water stable titanium compound, e.g., an organic titanium chelate such as the lactic acid chelate or the triethanolamine chelate, is present, the aqueous composition may be prepared long before application to the substrate. However, an acid or acid-generating compound is added to the aqueous composition shortly before application to the substrate. The resultant lowering of the pH promotes hydrolysis of the titanium compound, which may begin before or during application to the substrate. However, hydrolysis continues after said application and is followed by condensation of the TiOH groups generated thereby with the SiOH groups on the organopolysiloxane.

The rate of release of the insecticide may be controlled by adjusting the extent of crosslinking, e.g., by adjusting the polysiloxane/titanium ratio, the thickness of the polysiloxane coating, e.g., by modifying the concentration of reactive components in the solution thereof, or by adding a non-volatile, non-reactive extender for the crosslinked polysiloxane. The latter may be a hydrocarbon oil and acts in a manner analogous to the behavior of the hydrocarbon oil in a vulcanized oil-extended hydrocarbon rubber. The extender may be a compatible non-siloxane compound e.g., a hydrocarbon oil or may be an alkyl or arylpolysiloxane fluid having a viscosity ranging from 5 to 100,000 centistokes at 25° C.

In addition to or in lieu of the solvents which function to reduce the viscosity of the compositions of this invention as well as control the thickness of the polysiloxane coating, volatile alcohols such as ethanol, isopropanol, butanol and the like may be included in the composition to prevent premature hydrolysis of the hydrolyzable crosslinking agent with resultant gelation and precipitation.

Other additives which may be incorporated into the compositions of this invention include stabilizers against environmental degradation, such as antioxidants and ultraviolet stabilizers, odor masking compounds and perfumes, dyes, pigments, fillers, etc.

The following examples illustrate the best modes for carrying out this invention. Examples I and II illustrate the improved adhesion of the compositions of this invention to a substrate and Examples III to XIII illustrate the controlled release insecticidal effectiveness of the compositions of this invention. In the tables in the examples, the numbers refer to the amount of materials in parts by weight.

EXAMPLE I

Solutions cntaining 50 weight-% of one or more of the following components were prepared in anhydrous isooctane: (a) tetraisopropyl titanate (TPT), (b) a linear dimethylpolysiloxane fluid containing 3 weight-% hydroxyl groups and having a viscosity of 80 centistokes at 25° C., designated as Fl-3563 by the Dow Corning Corp., and (c) a dimethylpolysiloxane fluid, designated as a DC-200 fluid by the Dow Corning Corp., having a viscosity of 1000 centistokes at 25° C. (DC-200/1000).

The 50% solution was diluted to 10 weight-% with isooctane and 10-20 drops were placed on a weighed glass slide. A glass rod was rolled over the solution to spread the material uniformly over the lower four fifths of the slide. The coated slide was air dried for 4 hours and then placed in a 50% relative humidity chamber for 18 hours. The slide was then weighed to determine the weight of the coating which ranged from 2-5 mg. covering an area of 15 sq. cm. The coated slide was inserted into a slit rubber stopper and mounted over the center of a Waring Blender. The coated slide faced the moving water which completely covered the coating. The blender was operated at its highest speed for 5 minutes. The slide was air dried overnight and then weighed to determine the amount of coating retained on the slide after the treatment in the Blender. The average results of duplicate tests are summarized in Table 1.

Table 1

| | Adhesion of Titanate-Silanol Fl-3563 Compositions | | | |
|---|---|---|---|---|
| No. | TPT | Fl-3563 | DC-200/1000 | Retention, % |
| 1 | | | 100 | 44 |
| 2 | | 100 | | 28 |
| 3 | | 50 | 50 | 15 |
| 4 | 50 | 50 | | 90 |
| 5 | 33 | 33 | 33 | 95 |
| 6 | 20 | 80 | | 97 |

The adhesion of the coating composition, as measured by the retention, is greatly influenced by the presence and hydrolysis of the titanate. The crosslinking of the silanol as a result of the hydrolysis of the titanate results in a 90% or higher retention.

The 50% solutions of titanate, silanol and/or polysiloxane fluid in isooctane were mixed with a pyrethroid composition, as follows:
0.1 g. pyrethroids
0.5 g. piperonyl butoxide
0.4 g. petroleum distillate
5.0 g. 50% solution of TPT, Fl-3563 and/or DC-200/1000 in isooctane.

The pyrethroid-containing solutions were diluted to 10 weight-% with isooctane and coated on glass slides. The coated slides were dried, moisture cured and subjected to treatment with water in the Waring Blender, as described earlier. The amount of retained coating is summarized in Table 2, where the amount of pyrethroids indicated actually represents the sum of the pyrethroids and piperonyl butoxide.

Table 2

Adhesion of Pyrethroid-Titanate-Silanol Fl-3563 Compositions

| No. | TPT | Fl-3563 | DC-200/1000 | Pyrethroids | Retention, % |
|-----|-----|---------|-------------|-------------|--------------|
| 7   |     |         | 100         | 24          | 4            |
| 8   |     | 100     |             | 24          | 0            |
| 9   |     | 50      | 50          | 24          | 2            |
| 10  | 50  | 50      |             | 24          | 67           |
| 11  | 33  | 33      | 33          | 24          | 40           |

The effect of the titanate-silanol reaction is similar to that noted in the absence of the pyrethroids.

EXAMPLE II

Solutions containing 50 weight-% of one or more of the following components were prepared in anhydrous isooctane: (a) tetraisopropyl titanate (TPT), (b) a methylmethoxypolysiloxane fluid copolymer containing 30 weight-% methoxy groups and having a viscosity of 40 centistokes at 25° C., designated as F4-3597 by the Dow Corning Corp., and (c) a DC-200 fluid having a viscosity of 1000 centistokes at 25° C. (DC-200/1000).

The solutions were diluted, coated on glass slides, dried, moisture cured at 50% relative humidity for 18 hours and subjected to treatment with water in the Waring Blender, as described in Example I. The results are summarized in Table 3.

Table 3

Adhesion of Titanate-Methoxypolysiloxane Compositions

| No. | TPT | F4-3597 | DC-200/1000 | Retention, % |
|-----|-----|---------|-------------|--------------|
| 1   |     |         | 100         | 44           |
| 12  |     | 100     |             | 51           |
| 13  |     | 50      | 50          | 50           |
| 14  | 50  | 50      |             | 100          |
| 15  | 33  | 33      | 33          | 86           |

The effect of titanate crosslinking and adhesion promotion is clearly shown by the retention results. Similar results were obtained when pyrethroids were present.

EXAMPLE III

A silanol-titanate solution containing (a) a solid, branched methylsiloxane copolymer composed of trimethylsiloxane units and $SiO_2$ units with a $CH_3/Si$ ratio of 1.4 and containing 3 weight-% hydroxyl groups, designated as X2-5056 by the Dow Corning Corp., (b) tetraisopropyl titanate (TPT), and (c) a dimethylpolysiloxane fluid having a viscosity of about 10,000 centistokes at 25° C., designated DC-200/10,000, was prepared as a 50 weight-% solution in perchloroethylene. The components were present in the following proportions:

| Silanol-Titanate Solution III | |
|---|---|
| Silanol X2-5056 | 0.625 parts |
| TPT | 0.625 |
| DC-200/10,000 | 1.25 |
| Perchloroethylene | 2.50 |

A solution of Dypterex, i.e., O,O-dimethyl (2,2,2-trichloro-1-hydroxyethyl) phosphonate, was prepared for insecticidal evaluation. One portion of the Dypterex solution was blended with Silanol-Titanate Solution III while a second portion was evaluated without any additives. The components of the test solutions were as follows:

| | Insecticide Solution | |
|---|---|---|
| | IIIA | IIIB |
| Silanol-Titanate Solution III | 5.000 | — |
| Dypterex | 0.625 | 0.625 |
| Methylene Chloride | 40.000 | 40.000 |
| Isopropanol | 54.375 | 59.375 |

After 1 ml. of the test solution was spread by camel hair brush on a 6×6 inch piece of aluminum foil, the treated foil was maintained at ambient conditions for 24 hours. Ten adult male German cockroaches, *Blattella germanica* (Linnaeus) were exposed to the 1 day residue for 48 hours under a 100×15 mm. petri dish. The test was conducted in duplicate. The same treated foil was used in duplicate tests after 7 days and after 14 days.

The percent mortality of cockroaches exposed to the treated foil is summarized below:

| Insecticide Solution | | IIIA | IIIB |
|---|---|---|---|
| Residue age | 1 day | 100 | 100 |
| | 7 days | 100 | 100 |
| | 14 days | 55 | 0 |

Whereas the residue from the control insecticide solution IIIB failed to kill any cockroaches after 14 days, the residue from the insecticide solution IIIA, containing Silanol-Titanate Solution III, killed 55% of the exposed cockroaches after 14 days.

EXAMPLE IV

The insecticidal properties of the Dypterex insecticide solutions IIIA and IIIB from Example III were evaluated using adult houseflies *Musca domestica* Linnaeus as the test species.

After 1 ml. of the test solution was spread by camel hair brush on a 6×6 inch piece of aluminum foil, the treated foil was maintained at ambient conditions for 24 hours. Twenty adult houseflies were exposed to the 1 day residue for 3 hours under a 100×15 mm. petri dish. The test was conducted in duplicate. The same treated foil was used in duplicate tests after 7, 14, 21 and 28 days. In these tests the houseflies were exposed to the residue on the surface of the foil for 1 hour and then removed to caps with food.

The percent mortality of houseflies exposed to the treated foils is summarized below:

| Insecticide Solution | | IIIA | IIIB |
|---|---|---|---|
| Residue age | 1 day | 100 | 100 |
| | 7 days | 100 | 76 |
| | 14 days | 100 | 6 |
| | 21 days | 96 | 4 |
| | 28 days | 0 | 0 |

The residue from the control insecticide solution IIIB was essentially ineffective when the residue age was 14 days. However, the residue from the insecticide solution IIIA, containing Silanol-Titanate Solution III, still killed 96% of the exposed houseflies after 21 days.

EXAMPLE V

A solution of Baygon, i.e., 2-isopropoxyphenyl-N-methyl carbamate, was prepared for insecticidal evaluation. One portion of the Baygon solution was blended with the Silanol-Titanate Solution III of Example III containing Silanol X2-5056, TPT and DC-200/10,000. A second portion of the Baygon solution was evaluated without any additives. The components of the test solutions were as follows:

|  | Insecticide Solution | |
| --- | --- | --- |
|  | VA | VB |
| Silanol-Titanate Solution III | 5.00 | — |
| Baygon | 0.53 | 0.53 |
| Methylene chloride | 30.00 | 30.00 |
| Isopropanol | 64.47 | 69.47 |

The insecticidal properties of the Baygon insecticide solutions VA and VB were evaluated using adult houseflies as the test species and aluminum foil as the test surface, as described in Example IV.

The present mortality of houseflies exposed to the treated foils is summarized below:

| Insecticide Solution |  | VA | VB |
| --- | --- | --- | --- |
| Residue age | 1 day | 100 | 100 |
|  | 7 days | 94 | 98 |
|  | 14 days | 82 | 48 |
|  | 21 days | 2 | 0 |

Although the residue from the control insecticide solution VB killed only 48% of the houseflies after 14 days, the residue from the insecticide solution VA, containing Silanol-Titanate Solution III killed 82% of the exposed houseflies after 14 days.

EXAMPLE VI

The insecticidal properties of the Baygon insecticide solutions VA and VB from Example V were evaluated using German cockroaches as the test species and a 6×6 inch panel of painted plywood as the test surface. The test was conducted as described in Example III.

The percent mortality of cockroaches exposed to the treated painted plywood is summarized below.

| Insecticide Solution |  | VA | VB |
| --- | --- | --- | --- |
| Residue age | 1 day | 100 | 100 |
|  | 7 days | 95 | 65 |
|  | 14 days | 45 | 5 |
|  | 21 days | 15 | 0 |

The residue from the control insecticide solution VB killed only 65% of the cockroaches after 7 days and was essentially ineffective when the residue age was 14 days. In contrast, the residue from the insecticide solution VA containing Silanol-Titanate Solution III, killed 95% of the cockroaches after 7 days and was still active after 21 days.

EXAMPLE VII

An insecticidal solution was prepared from pyrethroids and various synergists and stabilizers. A portion of the solution was blended with Silanol-Titanate Solution III, from Example III, and a volatile silicone propellant, Union Carbide Volatile Silicone 7207, a dimethylpolysiloxane having a viscosity of 2.5 centistokes at 25° C. and a boiling point of 171° C. A second portion of the insecticidal solution was evaluated in the absence of any additives. The components of the test solutions were as follows:

|  | Insecticide Solution | |
| --- | --- | --- |
|  | VIIA | VIIB |
| Silanol-Titanate Solution III | 5.00 | — |
| Volatile Silicone 7207 | 5.00 | — |
| Pyrethroids | 0.10 | 0.10 |
| Piperonyl butoxide | 0.20 | 0.20 |
| N-Octylbicycloheptenedicarboximide (Synergist 264) | 0.33 | 0.33 |
| Butylated hydroxytoluene | 1.00 | 1.00 |
| Benzyl cinnamate | 2.00 | 2.00 |
| Petroleum distillate | 0.40 | 0.40 |
| Deodorized refined kerosene | 85.97 | 95.97 |

The insecticide solution was sprayed on aluminum foil so as to provide a coverage of 1.25 g. per 6×6 inch panel, i.e., 5 mg./sq. ft. Duplicate panels were treated and were allowed to age for 3 days before testing. Twenty five saw-toothed grain beetles, *Oryzaephilus surinamensis* (Linnaeus), were confined to the residue on the aluminum foil for 48 hours under a 100×15 mm. petri dish. The same treated foils were used after the residue had aged 7 days, 14 days, 21 days and 28 days.

The percent mortality of the beetles exposed to the treated foils is summarized below:

| Insecticide Solution |  | VIIA | VIIB |
| --- | --- | --- | --- |
| Residue age | 3 days | 100 | 100 |
|  | 7 days | 100 | 100 |
|  | 14 days | 100 | 100 |
|  | 21 days | 100 | 0 |
|  | 28 days | 28 | 0 |

Although the residue from the control insecticide solution VIIB was ineffective after 21 days, the residue from the insecticide solution VIIA, containing Silanol-Titanate Solution III, killed 100% of the exposed beetles after 21 days and still killed 28% of the beetles after 28 days.

EXAMPLE VIII

The insecticidal properties of the pyrethroid insecticide solutions VIIA and VIIB from Example VII were evaluated using twenty five confused flour beetles, *Tribolium confusum*, Jacquelin duVal, as the test species and aluminum foil as the test surface.

The test was conducted in duplicate in the same manner as described in Exmple VII. The beetles were exposed to the residues for 48 hours after the residues had been aged 3, 7, 14, 21 and 28 days.

The percent mortality of beetles exposed to the treated foils is summarized below:

| Insecticide Solution |  | VIIA | VIIB |
| --- | --- | --- | --- |
| Residue age | 3 days | 100 | 100 |
|  | 7 days | 100 | 100 |
|  | 14 days | 100 | 0 |
|  | 21 days | 100 | 0 |
|  | 28 days | 8 | 0 |

The residue from the control insecticide solution VIIB was ineffective after 14 days. The residue from the insecticide solution VIIA, containing Silanol-Titanate Solution III, killed 100% of the exposed beetles after 21 days and still had residual activity after 28 days.

EXAMPLE IX

An insecticidal solution was prepared from pyrethroids and synergists. A portion of the solution was blended with Silanol-Titanate Solution III, from Example III, and Volatile Silicone 7207. A second portion of the insecticidal solution was evaluated without any additives. The components of the test solutions were as follows:

|  | Insecticide Solution | |
| --- | --- | --- |
|  | IXA | IXB |
| Silanol-Titanate Solution III | 5.00 | — |
| Volatile Silicone 7207 | 5.00 | — |
| Pyrethroids | 0.10 | 0.10 |
| Piperonyl butoxide | 0.20 | 0.20 |
| Synergist 264 | 0.33 | 0.33 |
| Petroleum distillate | 0.40 | 0.40 |
| Isopropanol | 88.97 | 98.97 |

Detached dog hair was washed in Ivory Liquid and then rinsed with water and ethanol before air drying. Three gram quantities of the dog hair were placed in 9 cm. petri dishes and sprayed with a 5 ml. dosage of the test solutions using a Devilbiss atomizer with 6 p.s.i. air pressure. The dosage was sufficient to obtain good wetting without an excess of liquid. The treated hair was air dried for 6 hours and then transferred to one quart wide mouth mason jars.

Approximately 25 adult Oriental rat fleas, *Xenopsylla Cheopis* (Rothschild) were metered into each exposure jar and 100% mortality was recorded after 24 hours of exposure to the treated hair. The same results were obtained when the treated hair was aged 4 weeks and 6 weeks. After the treated hair was aged for 7 weeks, the hair was washed by stirring in 1000 ml. of water for 5 minutes. After drying, the hair was exposed to adult fleas for 24 hours and 100% mortality was recorded. The hair was again washed in 1000 ml. of water for 5 minutes. Since 100% mortality of the exposed fleas were again recorded, the treated hair was aged an additional week, i.e., a total of 8 weeks, washed in the same manner as the previous two washes, dried and exposed to the adult fleas for 24 hours. Again 100% mortality of exposed fleas was recorded. The treated hair was aged for two weeks, i.e., a total of 10 weeks, washed in 300 ml. of water on a wrist action shaker for 2 hours, dried and exposed to the adult fleas for 24 hours. The hair which had been treated with the control insecticide solution IXB killed 71% of the fleas while the hair which had been treated with insecticide solution IXA containing the silanol-titanate composition, killed 90% of the fleas. After another week of aging, i.e., a total of 11 weeks, the treated hair was washed in 300 ml. of water on a wrist action shaker for 1 hours, dried and exposed to adult fleas for 24 hours. The hair treated with control solution IXB killed 19% of the fleas while the hair treated with solution IXA killed 50% of the fleas. Untreated hair subjected to the same aging and washing treatments as the treated hair failed to kill any fleas at any time during the test cycle.

The percent mortality of fleas exposed to the treated hair is summarized below:

| Insecticide Solution | IXA | IXB |
| --- | --- | --- |
| Residue age |  |  |
| 7 weeks, wash 1 | 100 | 100 |
| 7 weeks, wash 2 | 100 | 100 |
| 8 weeks, wash 3 | 100 | 100 |
| 10 weeks, wash 4 | 90 | 71 |
| 11 weeks, wash 5 | 50 | 19 |

EXAMPLE X

A solution containing 50 weight-% non-volatiles was prepared as follows:
- 10 g. tetraisopropyl titanate (TPT)
- 10 g. methylmethoxypolysiloxane F4-3597 (30 wt-% $OCH_3$)
- 10 g. DC-200/1000 dimethylpolysiloxane fluid
- 30 g. perchloroethylene The titanate-methylmethoxypolysiloxane-polysiloxane fluid solution was mixed with a pyrethroid composition to yield an insecticide-containing solution which was compared with an additive-free pyrethroid composition for insecticidal behavoir. The components of the test compositions were as follows:

|  | Insecticide Solution | |
| --- | --- | --- |
|  | X A | X B |
| Pyrethroids | 0.1 | 0.1 |
| Piperonyl butoxide | 0.5 | 0.5 |
| Petroleum distillate | 49.4 | 99.4 |
| TPT | 8.33 | — |
| F4-3597 | 8.33 | — |
| DC-200/1000 | 8.33 | — |
| Perchloroethylene | 25.01 | — |

A disposable plastic syringe was used to place the test solution on a 4×4 inch glass panel. The solution was uniformly spread over the panel with the tip of the syringe. The treated panels were conditioned for 24 hours in a chamber at 78° F. and 42% relative humidity. Ten adult male German cockroaches, *Blattella germanica* (Linnaeus), were exposed to the 1 day residue for 24 hours under a 100×15 mm. petri dish. The test was conducted in duplicate. The same treated panels were reexposed to cockroaches after 3, 7 and 10 days.

The percent mortality of cockroaches exposed to the treated glass panels is summarized below:

| Insecticidal Solution | XA | XB |
| --- | --- | --- |
| Residue age |  |  |
| 1 day | 85 | 100 |
| 3 days | 95 | 100 |
| 7 days | 50 | 5 |
| 10 days | 70 | 0 |

The residue from the control insecticide solution XB was ineffective and killed only 5% of the exposed cockroaches after 7 days while the residue from insecticide solution XA, containing titanate-methylmethoxypolysiloxane-dimethylpolysiloxane fluid composition, killed 50% of the exposed cockroaches after 7 days and 70% after 10 days.

The panel containing the 11 days old residue from solution XA was then subjected to the vigorous action of water in a Waring Blender for 5 minutes, as described in Example I. The water-treated panels were maintained under ambient conditions and then reexposed to cockroaches after 5 days (residue age 16 days) and 10 days (residue age 21 days).

The percent mortality of cockroaches exposed to the washed panels was as follows:

| Insecticide Solution | XA |
|---|---|
| Residue Age (washed after 11 days) | |
| 16 days | 85 |
| 21 days | 75 |

Despite the water treatment, the residue from solution XA was still highly effective after 21 days.

EXAMPLE XI

The same composition as in Example X was prepared using isooctane as solvent instead of perchloroethylene, as follows:
 10 g. tetraisopropyl titanate (TPT)
 10 g. F4-3597 (30 wt-% OCH$_3$)
 10 g. DC-200/1000
 30 g. isooctane The solution was mixed with a pyrethroid composition to yield an insecticide solution which was compared with the pyrethroid solution per se for insecticidal properties. The components of the test solutions were as follows:

| | Insecticide Solution | |
|---|---|---|
| | XIA | XIB |
| Pyrethroids | 0.1 | 0.1 |
| Piperonyl butoxide | 0.5 | 0.5 |
| Petroleum distillate | 49.4 | 99.4 |
| TPT | 8.33 | — |
| F4-3597 | 8.33 | — |
| DC-200/1000 | 8.33 | — |
| Isooctane | 25.01 | — |

The insecticidal properties of solutions XIA and XIB were evaluated using adult cockroaches as the test species and glass as the test surface, as described in Example X. The treated glass panels were exposed, in duplicate, to cockroaches after 1, 3, 7 and 10 days. On the 11th day the panel containing the residue from solution XIA was subjected to treatment with water in a Waring Blender for 5 minutes, as described in Example I, and then reexposed to cockroaches after a total of 16 days and 21 days.

The percent mortality of cockroaches exposed to the treated glass panels is summarized below:

| Insecticidal Solution | XIA | XIB |
|---|---|---|
| Residue age | | |
| 1 day | 100 | 100 |
| 3 days | 100 | 100 |
| 7 days | 85 | 5 |
| 10 days | 80 | 0 |
| 11 days (water treatment) | | |
| 16 days | 45 | |
| 21 days | 45 | |

Although the residue from the control insecticide solution XIB was ineffective after 7 days, the insecticide solution XIA, containing the titanate-methoxypolysiloxane-dimethylpolysiloxane fluid composition, was still effective after 21 days, despite a water treatment after 11 days.

EXAMPLE XII

A solution containing 50 weight-% non-volatiles was prepared as follows:
 15 g. tetraisopropyl titanate (TPT)
 15 g. dimethylpolysiloxane Fl-3563 (3 wt-% OH)
 30 g. perchloroethylene The titanate-polysiloxane solution was mixed with a pyrethroid composition to yield an insecticide-containing solution which was compared with an additive-free pyrethroid composition for insecticidal behavior. The components of the test compositions were as follows:

| | Insecticide Solution | |
|---|---|---|
| | XIIA | XIIB |
| Pyrethroids | 0.1 | 0.1 |
| Piperonyl butoxide | 0.5 | 0.5 |
| Petroleum distillate | 0.4 | 0.4 |
| TPT | 0.5 | — |
| Fl-3563 | 0.5 | — |
| Perchloroethylene | 98.0 | 99.0 |

The insecticidal properties of solutions XIIA and XIIB were evaluated using adult cockroaches as the test species and glass as the test surface, as described in Example X. The treated glass panels were exposed, in duplicate, to cockroaches after 1, 3, 7, and 10 days.

The percent mortality of cockroaches exposed to the treated glass panels is summarized below:

| Insecticidal Solution | XIIA | XIIB |
|---|---|---|
| Residue age | | |
| 1 day | 100 | 100 |
| 3 days | 100 | 100 |
| 7 days | 80 | 15 |
| 10 days | 5 | 0 |

The residue from the control insecticide solution XIIB killed 15% of the exposed cockroaches after 7 days while the residue from the insecticide solution XIIA, containing the titanate-polysiloxane composition, did not become inactive until the residue age was 10 days.

EXAMPLE XIII

A solution containing 50 weight-% non-volatiles was prepared as follows:
 10 g. tetraisopropyl titanate (TPT)
 10 g. siloxane copolymer X2-5056 with (CH$_3$)$_3$SiO and SiO$_2$ groups (3 wt-% OH)
 10 g. DC-200/1000 dimethylpolysiloxane fluid
 30 g. perchloroethylene The titanate-siloxane copolymer-dimethylpolysiloxane solution was mixed with a pyrethroid composition to yield an insecticide-containing solution which was compared with an additive-free pyrethroid composition for insecticidal behavior. The components of the test composition were as follows:

| | Insecticide Solution | |
|---|---|---|
| | XIIIA | XIIIB |
| Pyrethroids | 0.1 | 0.1 |
| Piperonyl butoxide | 0.5 | 0.5 |
| Petroleum distillate | 0.4 | 0.4 |
| TPT | 0.33 | — |
| X2-5056 | 0.33 | — |
| DC-200/1000 | 0.33 | — |

-continued

|  | Insecticide Solution | |
|---|---|---|
|  | XIIIA | XIIIB |
| Perchloroethylene | 98.01 | 99.0 |

The insecticidal properties of solutions XIIIA and XIIIB were evaluated using adult cockroaches as the test species and glass as the test surface, as described in Example X. The treated glass panels were exposed, in duplicate, to cockroaches after 1, 3, 7 and 10 days.

The percent mortality of cockroaches exposed to the treated glass panels is summarized below:

| Insecticidal Solution | XIIIA | XIIIB |
|---|---|---|
| Residue age | | |
| 1 day | 100 | 100 |
| 3 days | 100 | 100 |
| 7 days | 95 | 15 |
| 10 days | 5 | 0 |

The residue from the control insecticide solution XIIIB killed 15% of the exposed cockroaches after 7 days while the residue from solution XIIIA, containing the titanate-siloxane copolymer-polysiloxane mixture killed 95% of the exposed cockroaches after 7 days.

EXAMPLE XIV

A solution containing 50 weight-% non-volatiles was prepared as follows:
 5 g. tetrabutyl titanate (TBT)
 45 g. dimethylpolysiloxane Fl-3563 (3 wt-% OH)
 50 g. perchloroethylene The titanate-polysiloxane solution was mixed with a pyrethroid composition to yield an insecticide-containing solution which was compared with an additive-free pyrethroid composition for insecticidal behavior. The components of the test compositions were as follows:

|  | Insecticide Solution | | |
|---|---|---|---|
|  | XIVA | XIVB | XIVC |
| Pyrethroids | 0.1 | 0.1 | 0.1 |
| Piperonyl butoxide | 0.5 | 0.5 | 0.5 |
| Petroleum distillate | 0.4 | 0.4 | 0.4 |
| TBT | 0.5 | 0.25 | — |
| Fl-3563 | 4.5 | 2.25 | — |
| Perchloroethylene | 94.0 | 96.5 | 99.0 |

The insecticidal properties of solutions XIVA, XIVB and XIVC were evaluated using adult cockroaches as the test species and glass as the test surface, as described in Example X. The treated glass panels were exposed, in duplicate, to cockroaches after 1, 3, 7 and 10 days.

The percent mortality of cockroaches exposed to the treated glass panels is summarized below:

| Insecticide solution | XIVA | XIVB | XIVC |
|---|---|---|---|
| Residue age | | | |
| 1 day | 100 | 100 | 100 |
| 3 days | 100 | 100 | 100 |
| 7 days | 80 | 85 | 0 |
| 10 days | 85 | 85 | 0 |

The residue from the control insecticide solution XIVC was ineffective on the 7th day while the residues from insecticide solutions XIVA and XIVB containing the titanate-polysiloxane compositions killed 85% of the exposed cockroaches after 10 days.

On the 11th day the panels containing the residues from solutions XIVA and XIVB were subjected to treatment with water in a Waring Blender for 5 min., as described in Example I, and then reexposed to cockroaches after a total residue age of 14 days and 21 days.

The percent mortality of cockroaches exposed to the treated glass panels is summarized below:

| Insecticide Solution | XIVA | XIVB |
|---|---|---|
| Residue Age | | |
| 11 days (water treatment) | | |
| 14 days | 50 | 5 |
| 21 days | 40 | |

EXAMPLE XV

A solution containing 33 weight-% non-volatiles was prepared as follows:
 10 g. tetraisopropyl titanate (TPT)
 10 g. branched propylphenylpolysiloxane (6 wt-% OH) (Z-6018), Dow Corning Corp.
 20 g. perchloroethylene
 20 g. isopropyl alcohol The titanate-polysiloxane solution was mixed with 1-naphthyl N-methylcarbamate (Carbaryl) to yield an insecticide-containing solution which was compared with an additive-free Carbaryl composition for insecticidal behavior. The components of the test compositions were as follows:

|  | Insecticide Solution | |
|---|---|---|
|  | XVA | XVA |
| Carbaryl | 0.5 | 0.5 |
| TPT | 0.835 | — |
| Z-6018 | 0.835 | — |
| Perchloroethylene | 1.67 | — |
| Isopropyl alcohol | 96.16 | 99.5 |

The test compositions were applied to upper and lower leaf surfaces of potted lima bean plants with a DeVilbiss atomizer from a distance of 30.5 millimeters. There were two plants per pot, with leaves approximately 50–60 mm. wide and 70–80 mm. long. A 3.2 ml. application was sprayed evenly over the two potted plants at 3 psi pressure. The treated plants were kept in a chamber at 80° F. and 55% relative humidity. After 12 days the treated plants were sprayed with one-half inch of tap water from a hose end sprayette #4 nozzle held at a distance of 18 inches for a period of 5–10 minutes. Two leaves were removed from the sprayed potted plants and exposed to ten Southern army worm larvae (late third instar) on the 14th day for 48 hours.

The leaves which had been sprayed with insecticide solution XVA, containing the titanate-polysiloxane composition, killed 100% of the larvae while the leaves which had been sprayed with the control insecticide solution XVB were ineffective and there was 0% mortality of the exposed larvae.

When the leaves of the treated and sprayed plants were exposed to ten Mexican bean beetle larvae (late second instar), the results were the same, i.e., the leaves sprayed with insecticide solution XVA killed 100% of the larvae while the leaves which had been sprayed with the control insecticide solution XVB killed none of the exposed larvae.

EXAMPLE XVI

The titanate-polysiloxane solution of Example XV was mixed with S-(1,2-dicarbethoxyethyl)0,0-dimethyl dithiophosphate (Malathion) to yield an insecticide solution which was compared with an additive-free Malathion composition. The components of the test compositions were as follows:

|  | Insecticide Solution | |
|---|---|---|
|  | XVIA | XVIB |
| Malathion | 0.5 | 0.5 |
| TPT | 0.835 | — |
| Z-6018 | 0.835 | — |
| Perchloroethylene | 1.67 | — |
| Isopropyl alcohol | 96.16 | 99.5 |

The insecticidal properties of solutions XVIA and XVIB were evaluated using ten Mexican bean beetle larvae (late second instar) as the test species and potted lima bean plants as the test substrate, as described in Example XV. The treated plants were sprayed with water after 12 days and exposed to the larvae after 14 days, as described in Example XV.

The leaves which had been sprayed with insecticide solution XVIA, containing the titanate-polysiloxane composition, killed 90% of the larvae while the leaves which had been sprayed with the control insecticide solution XVIB killed only 40% of the exposed larvae.

What is claimed is:

1. A composition consisting essentially of (a) an organopolysiloxane, soluble in organic solvents, and containing hydroxyl groups or functional groups which are hydrolyzable to hydroxyl groups, (b) a hydrolyzable titanium compound or a partial hydrolyzate thereof wherein said titanium compound is selected from the group consisting of tetraesters, tetraanhydrides, tetraamides and chelates of glycols, hydroxyacids, dicarboxylic acids, diketones, ketoesters and alkanolamines, and (c) an insecticide, said composition being capable of in situ formation of a polymeric coating.

2. The composition of claim 1 wherein the organopolysiloxane contains the structural unit

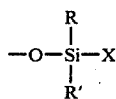

wherein X is a hydroxyl radical or a hydrolyzable radical and R and R' are oxygen or non-hydrolyzable hydrocarbon or heterocyclic radicals.

3. The composition of claim 1 wherein the hydrolyzable groups on the organopolysiloxane are selected from the group consisting of halogen, alkoxy, acyloxy and hydrogen.

4. The composition of claim 2 wherein the non-hydrolyzable hydrocarbon radicals are selected from the group consisting of branched, linear or cyclic aliphatic radicals, aromatic radicals, aralkyl radicals and alkylaryl radicals.

5. The composition of claim 1 wherein the weight ratio of (a) and (b) is within the range 10/90 to 95/5.

6. A composition consisting essentially of (a) an organopolysiloxane, soluble in organic solvents, and containing hydroxyl groups or functional groups which are hydrolyzable to hydroxyl groups, (b) a hydrolyzable organic titanium compound or a partial hydrolyzate thereof wherein said titanium compound is selected from the group consisting of tetraesters, tetraanhydrides, tetraamides and chelates of glycols, hydroxyacids, dicarboxylic acids, diketones, ketoesters and alkanolamines, (c) a non-volatile, non-reactive hydrocarbon oil or organopolysiloxane, and (d) an insecticide, wherein the weight ratio of (a) and (b) is within the range of 10/90 to 95/5, said compositions being capable of in situ formation of a polymeric coating.

7. A composition consisting essentially of (a) an organopolysiloxane, soluble in organic solvents, and containing hydroxyl groups or functional groups which are hydrolyzable to hydroxyl groups, (b) a hydrolyzable organic titanium compound or a partial hydrolyzate thereof wherein said titanium compound is selected from the group consisting of tetraesters, tetraanhydrides, tetraamides and chelates of glycols, hydroxyacids, dicarboxylic acids, diketones, ketoesters and alkanolamines, (c) an insecticide, and (d) a volatile diluent selected from the group consisting of aliphatic or aromatic hydrocarbons, halogenated hydrocarbons, organopolysiloxane fluids and water, wherein the weight ratio of (a) and (b) is within the range of 10/90 to 95/5, said compositions being capable of in situ formation of a polymeric coating.

8. A composition consisting essentially of (a) an organopolysiloxane, soluble in organic solvents, and containing hydroxyl groups or functional groups which are hydrolyzable to hydroxyl groups, (b) a hydrolyzable organic titanium compound or a partial hydrolyzate thereof wherein said titanium compound is selected from the group consisting of tetraesters, tetraanhydrides, tetraamides and chelates of glycols, hydroxyacids, dicarboxylic acids, diketones, ketoesters and alkanolamines, (c) a non-volatile, non-reactive hydrocarbon oil or organopolysiloxane, (d) an insecticide, and (e) a volatile diluent selected from the group consisting of aliphatic or aromatic hydrocarbons, halogenated hydrocarbons, organopolysiloxane fluids and water, wherein the weight ratio of (a) and (b) is within the range of 10/90 to 95/5, said composition being capable of in situ formation of a polymeric coating.

9. A process for providing a substrate containing active hydrogen atoms with an adherent controlled release pesticide which comprises applying the composition of claim 1 to said substrate and exposing the coated substrate to atmospheric moisture.

10. A process for providing a substrate containing active hydrogen atoms with an adherent controlled release pesticide which comprises applying the composition of claim 2 to said substrate and exposing the coated substrate to atmospheric moisture.

11. A process for providing a substrate containing active hydrogen atoms with an adherent controlled release pesticide which comprises applying the composition of claim 3 to said substrate and exposing the coated substrate to atmospheric moisture.

12. A process for providing a substrate containing active hydrogen atoms with an adherent controlled release pesticide which comprises applying the composition of claim 4 to said substrate and exposing the coated substrate to atmospheric moisture.

13. A process for providing a substrate containing active hydrogen atoms with an adherent controlled release pesticide which comprises applying the composition of claim 5 to said substrate and exposing the coated substrate to atmospheric moisture.

14. A process for providing a substrate containing active hydrogen atoms with an adherent controlled release pesticide which comprises applying the composition of claim 6 to said substrate and exposing the coated substrate to atmospheric moisture.

15. A process for providing a substrate containing active hydrogen atoms with an adherent controlled release pesticide which comprises applying the composition of claim 7 to said substrate and exposing the coated substrate to atmospheric moisture.

16. A process for providing a substrate containing active hydrogen atoms with an adherent controlled release pesticide which comprises applying the composition of claim 8 to said substrate and exposing the coated substrate to atmospheric moisture.

17. A process as defined in claim 9 wherein said substrate is a plant.

18. A process as defined in claim 9 wherein said substrate is an animal.

19. A process as defined in claim 9 wherein said substrate is the surface of a structure.

* * * * *